United States Patent
Zhang et al.

(10) Patent No.: US 10,918,580 B2
(45) Date of Patent: Feb. 16, 2021

(54) ORAL CARE COMPOSITIONS AND METHODS

(71) Applicant: Colgate-Palmolive Company, New York, NY (US)

(72) Inventors: Shaoyi Zhang, Highland Park, NJ (US); Saide Tang, Princeton, NJ (US); Carl Myers, Wayne, NJ (US); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/840,857

(22) Filed: Apr. 6, 2020

(65) Prior Publication Data

US 2021/0000709 A1    Jan. 7, 2021

Related U.S. Application Data

(60) Provisional application No. 62/869,394, filed on Jul. 1, 2019.

(51) Int. Cl.

| | | |
|---|---|---|
| *A61K 8/21* | (2006.01) | |
| *A61K 8/20* | (2006.01) | |
| *A61K 8/19* | (2006.01) | |
| *A61Q 11/00* | (2006.01) | |
| *A61K 8/41* | (2006.01) | |
| *A61K 8/55* | (2006.01) | |
| *A61K 8/27* | (2006.01) | |

(52) U.S. Cl.
CPC .................. *A61K 8/21* (2013.01); *A61K 8/19* (2013.01); *A61K 8/20* (2013.01); *A61K 8/27* (2013.01); *A61K 8/416* (2013.01); *A61K 8/55* (2013.01); *A61Q 11/00* (2013.01)

(58) Field of Classification Search
None
See application file for complete search history.

(56) References Cited

U.S. PATENT DOCUMENTS

| | | |
|---|---|---|
| 5,352,439 A | 10/1994 | Norfleet et al. |
| 5,693,314 A | 12/1997 | Campbell et al. |
| 5,811,079 A | 9/1998 | Yu et al. |
| 6,464,963 B1 | 10/2002 | Gambogi et al. |
| 8,926,950 B2 | 1/2015 | Heckendorn et al. |
| 9,937,115 B2 * | 4/2018 | Haught .................. A61Q 11/00 |
| 9,968,803 B2 | 5/2018 | Fruge et al. |
| 2011/0020247 A1 | 1/2011 | Strand |
| 2017/0281486 A1 | 10/2017 | Midha et al. |
| 2018/0177695 A1 | 6/2018 | Miller et al. |

FOREIGN PATENT DOCUMENTS

| | | |
|---|---|---|
| WO | 2017/117363 | 7/2017 |

OTHER PUBLICATIONS

Campbell, 1954, "A kinetic study of the hydrolysis of pyrophosphates," Journal of the American Chemical Society 76(3):893-901.
Myers et al., 2019, "Solving the problem with stannous fluoride," Journal of the American Dental Association 150(4 Suppl.):S5-S13.
Anonymous, 2000, "Toothpaste Extension", Mintel Database GNPD AN: 10076005.
Anonymous, 2002, "Flouride Toothpaste for Sensitive Teeth", Mintel Database GNPD AN: 10111837.
International Search Report and the Written Opinion of the International Searching Authority issued in International Application PCT/US2020/026844 dated Jul. 21, 2020.

* cited by examiner

*Primary Examiner* — Nannette Holloman

(57) ABSTRACT

This application relates to novel aqueous oral care compositions useful for combining and delivering incompatible stannous fluoride or stannous chloride and potassium salts in a high-water composition, for example, to provide effective caries prevention, protection against dental erosion, and relief from dental hypersensitivity. The compositions comprise stannous fluoride or stannous chloride, nitric acid or a water-soluble nitrate salt, a water-soluble alkali metal polyphosphate and more than 10% water, by weight of the composition.

15 Claims, No Drawings

ORAL CARE COMPOSITIONS AND METHODS

CROSS-REFERENCE TO RELATED APPLICATIONS

This application is a United States application filed under 35 U.S.C. § 111(a) claiming priority to and the benefit of U.S. Provisional Application No. 62/869,394, filed on Jul. 1, 2019, the contents of which are hereby incorporated by reference in its entirety.

BACKGROUND

This application relates to novel aqueous oral care compositions useful for combining and delivering incompatible stannous fluoride or stannous chloride and potassium salts in a high-water composition, for example, to provide effective caries prevention, protection against dental erosion, and relief from dental hypersensitivity.

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Oral care compositions which contain stannous ion sources exhibit excellent clinical benefits, particularly in the reduction of gingivitis. Stannous ion sources, such as stannous fluoride and stannous chloride, are well known for use in clinical dentistry with a history of therapeutic benefits over forty years. However, until recently, its popularity has been limited by its instability in aqueous solutions. The instability of stannous salts in water is primarily due to the reactivity of the stannous ion ($Sn^{2+}$). Stannous salts readily hydrolyze at a pH above 4, resulting in precipitation from solution. It has traditionally been thought that this formation of insoluble stannous salts results in a loss of therapeutic properties.

One common way to overcome the stability problems associated with stannous ions is to limit the amount of water in the composition to very low levels, or to use a dual phase system. Both of these solutions to the stannous ion problem have drawbacks. Low water oral care compositions can be difficult to formulate with desired rheological properties, and dual-phase compositions are considerably more expensive to manufacture and package. Thus, it is preferable to formulate a high-water composition which uses an alternative means to maintain stable efficacious stannous ion concentrations.

Dentinal hypersensitivity (i.e. sensitivity) is a painful condition resulting from the movement of liquid in exposed dentin tubules from external stimuli such as pressure and temperature.

Toothpastes fighting sensitive teeth (dentinal hypersensitivity) often contain the salt potassium nitrate. See, e.g., Norfleet et al., U.S. Pat. No. 5,352,439 (Colgate-Palmolive Co.). However, this ingredient is well known to have foam breaking properties making it difficult to obtain the sensory foam profile which delivers improved consumer acceptance. In many regions of the world, consumers prefer high foaming toothpastes over products that have a poor foaming ability. Conventional levels of surfactants usually yield acceptable foam volumes when tested in pure water. However, when the testing is performed in solutions mimicking the composition of human saliva it is hard to achieve foam levels that exceed a certain volume as also human saliva has foam breaking properties.

Formulation of oral care compositions comprising stannous fluoride or stannous chloride and potassium salts is particularly challenging because of stability issues between these two ingredients. Gambogi et al., U.S. Pat. No. 6,464,963 (Colgate-Palmolive Co.), discloses that attempts to include both stannous fluoride and potassium salts, such as potassium nitrate, in a single-phase, desensitizing dental composition is hampered by the formation of insoluble stannic salts and compounds such as $Sn(OH)_2$ and $SnO_2$. Gambogi solves this problem by resorting to dual-component compositions in which one component comprises the potassium salt, along with sodium hydroxide to adjust the pH of the component to 8 to 11, and the second component comprises the stannous fluoride or other stannous salts. These compositions also contain no more than 40% water. Other suggestions in the prior art for formulations combining fluoride and stannous salts similarly call for very low water contents, e.g., less than 10% water. See, e.g., Fruge et al., U.S. Pat. No. 9,968,803 (Colgate-Palmolive Co.).

It has also been reported that aqueous oral care compositions comprising unstabilized stannous ion and nitrate ion together may form potentially toxic species such as nitrite ion and nitrosamines, due to the reduction of the nitrate ion by the stannous ion. See, e.g., Campbell et al., U.S. Pat. No. 5,693,314 (Colgate-Palmolive Co.); Strand, US 2011/0020247 (Procter & Gamble Co.); Heckendorn et al., U.S. Pat. No. 8,926,950 (GABA Int'l Holding). To avoid this issue, Campbell resorts to a two-component composition with the stannous ion source and the nitrate ion source in separate components. Heckendorn resolves this problem in a single-phase aqueous composition by strictly controlling the molar ratio of solvated nitrate ion to solvated stannous ion of less than 2:1 at a pH of 3 to 6. Strand resolves this problem in a single-phase composition by stabilizing the stannous ion with a chelant, such as citric acid or polyphosphates such as tripolyphosphate, in moderate water compositions (e.g., 20-65% water), Strand also reports the further difficulty that fluoride ions in an oral care composition tend to precipitate out of solution when potassium nitrate is present, due to the low solubility of ionic fluoride sources. Strand solves this problem by using monofluorophosphate salts rather than fluoride salts as fluoride ion sources.

While it has been generally suggested that oral care compositions comprising stannous salts, fluoride salts, and polyphosphate could be prepared, many references do not take issue with or seem to be aware of the unique formulation difficulties which may be encountered. See, e.g., Yu et al., U.S. Pat. No. 5,811,079 (Warner-Lambert Co.); Midha et al., US 2017/0281486 (Procter & Gamble Co.). Other reference disclosing similar compositions avoid the issues by resorting to dual-component manufactures. See, e.g., Miller et al., US 2018/0177695 (Colgate-Palmolive Co.).

There is thus a need for novel oral compositions and methods that provide stable formulations of stannous fluoride or stannous chloride and potassium salts.

BRIEF SUMMARY

It is surprisingly found that a combination of stannous fluoride or stannous chloride, nitric acid or a soluble nitrate salt, and an alkali metal polyphosphate salt in high-water oral care composition results in stability of stannous, fluoride and nitrate in solution. Preferably, the nitrate salt is an alkali metal nitrate (e.g., potassium nitrate) and the alkali metal polyphosphate is a pyrophosphate, tripolyphosphate, tetraphosphate or hexametaphosphate (e.g., sodium or potassium pyrophosphate). In some embodiments, the composition comprises at least 10% water, e.g., at least 50% or at least 75% w/w of water. In some embodiments, the composition has a pH above 6.0, e.g., of about 7. Preferably the composition is a mouthwash.

The disclosure further provides methods of stabilizing stannous ion in an aqueous oral care composition formulating the composition with a nitrate ion source (e.g., potassium nitrate) and a polyphosphate ion source (e.g., sodium or potassium pyrophosphate) in a high-water composition (e.g., at least 10% w/w of water), optionally wherein the solution has a pH above 6.0 (e.g., about 7).

It is also surprisingly found that the stabilization of stannous using nitrate and polyphosphate according to the present disclosure can result in extremely clear and translucent toothpaste and gel compositions, which is a significant advance in toothpaste aesthetics.

The disclosure further provides single-component oral care composition packages comprising the compositions disclosed herein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

In a first aspect, the present disclosure provides a single-component oral care composition (Composition 1) comprising:
  (i) stannous fluoride or stannous chloride;
  (ii) nitric acid or a water-soluble nitrate salt (e.g., potassium nitrate);
  (iii) a water-soluble alkali metal polyphosphate (e.g., sodium or potassium pyrophosphate or tripolyphosphate); and
  (iv) more than 10% water, by weight of the composition.

For example, the disclosure provides embodiments of Composition 1 as follows:
  1.1 Composition 1, wherein the water-soluble nitrate salt is selected from an alkali or alkaline earth metal nitrate, or zinc nitrate, silver nitrate, or ammonium nitrate.
  1.2 Composition 1.1, wherein the water-soluble nitrate salt is an alkali metal nitrate salt or an alkaline earth metal nitrate salt.
  1.3 Composition 1.2, wherein the nitrate salt is selected from lithium nitrate, sodium nitrate, potassium nitrate, magnesium nitrate, and calcium nitrate.
  1.4 Composition 1.3, wherein the nitrate salt is potassium nitrate.
  1.5 Any foregoing composition, wherein the water-soluble alkali metal polyphosphate is selected from a pyrophosphate, tripolyphosphate, tetraphosphate or hexametaphosphate.
  1.6 Any foregoing composition, wherein the water-soluble alkali metal polyphosphate is a sodium or potassium polyphosphate.
  1.7 Any foregoing composition, wherein the water-soluble alkali metal polyphosphate is selected from sodium pyrophosphate, potassium pyrophosphate, sodium tripolyphosphate and potassium tripolyphosphate.
  1.8 Composition 1.7, wherein the sodium pyrophosphate salt is selected from sodium acid pyrophosphate (i.e., disodium pyrophosphate) and tetrasodium pyrophosphate.
  1.9 Any foregoing composition, wherein the water-soluble nitrate salt is potassium nitrate and the water-soluble alkali metal polyphosphate salt is tetrasodium pyrophosphate.
  1.10 Any foregoing composition, wherein the composition comprises a molar ratio of alkali metal polyphosphate (e.g., tetrasodium pyrophosphate) to stannous fluoride or stannous chloride of at least 1:1, e.g., 1:1 to 5:1, or 1:1 to 4:1, or 1:1 to 3:1, or 1:1 to 2:1, or 1.5:1 to 5:1, or 2:1 to 5:1, or 2:1 to 4:1, or 2:1 to 3:1, or about 1:1.
  1.11 Any foregoing composition, wherein the composition comprises a molar ratio of nitric acid or water-soluble nitrate salt (e.g., potassium nitrate) to stannous fluoride or stannous chloride of at least 0.3:1, e.g., 0.3:1 to 20:1, or 0.5:1 to 20:1, or 1:1 to 20:1, or 1:1 to 15:1, or 1:1 to 10:1, or 1:1 to 5:1 or 1:1 to 3:1, or about 1:1.
  1.12 Any foregoing composition, wherein the composition comprises from 0.1 to 2% stannous fluoride or stannous chloride, by weight of the composition, e.g., 0.1 to 1%, or 0.25 to 0.75%, or about 0.45%.
  1.13 Any foregoing composition, wherein the composition comprises from 0.1 to 5% of the nitric acid or water-soluble nitrate salt (e.g., potassium nitrate), by weight of the composition, e.g., 0.1 to 2%, or 0.1 to 1%, or 0.1 to 0.5%, or 0.2 to 0.4%, or 0.25 to 0.75%, about 0.3%, or about 0.5%.
  1.14 Any foregoing composition, wherein the composition comprises from 0.1 to 5% of the alkali metal polyphosphate salt (e.g., tetrasodium pyrophosphate or sodium tripolyphosphate), by weight of the composition, e.g., 0.8 to 5%, or 0.8 to 4%, or 0.8 to 3%, or 0.8 to 2%, or 0.8 to 1.0%, or 1.0 to 1.5%, or about 0.8%, or about 1.2%.
  1.15 Any foregoing composition, wherein the composition comprises at least 10% water by weight of the composition, e.g., at least 20%, at least 30%, or at least 40%, or at least 50%, or at least 60% or at least 65%, up to 95% water, by weight of the composition, or about 20%, or about 30%, or about 40%, or about 60% or about 80%.

1.16 Any foregoing composition wherein the composition comprises 70% to 95% water, by weight of the composition, e.g., from 75% to 95%, or from 75% to 90%, or from 75% to 85%, or from 75% to 80%; or wherein the composition comprises from 10% to 50% water, by weight of the composition, e.g., 10% to 40%, or 10% to 30%, or about 20%.

1.17 Any foregoing composition, wherein the composition comprises one or more humectants (e.g., glycerin, sorbitol, propylene glycol, or a mixture thereof) in a net amount of 5% to 70% by weight of the composition, e.g., from 5% to 25% by weight of the composition, or from 10% to 25%, or from 15% to 25%, or about 20%, or from 30 to 70%, or from 35 to 60%, or from 40 to 60%, or from 60 to 70%, by weight of the composition.

1.18 Any foregoing composition, wherein the composition is a single phase, i.e., it does not form two phases on standing.

1.19 Any foregoing composition, wherein the composition is dual phase, i.e., it forms two phases on standing.

1.20 Composition 1.19, wherein the composition forms an emulsion immediately upon mixing, and separates into two phases upon standing within 10 minutes (e.g., within 5 minutes, or within 3 minutes, or within 1 minute).

1.21 Any foregoing composition, wherein the composition is a clear (e.g., not opaque or turbid) solution (e.g., not a suspension) or a clear (e.g., translucent, not opaque) semisolid or gel.

1.22 Any foregoing composition, wherein the composition is physically and chemically stable, for example, wherein no color change or precipitation occurs on storage at ambient conditions for 3 months or more (e.g., 6 months or more, or 1 year or more).

1.23 Composition 1.22, wherein the stannous ion concentration is substantially stable for at least three months on storage, e.g., the concentration of stannous ion is at least 80% of the original concentration, or at least 85%, or at least 90%.

1.24 Any foregoing composition, wherein the composition has a pH of between 5 and 9, or a pH between 6 and 8, or a pH between 6.5 and 7.5, or a pH between 6.9 and 7.1, or a pH of about 7.

1.25 Any foregoing composition, wherein the composition comprises less than 10% of any hydrophobic liquid or mixture of hydrophobic liquids (e.g., alkyl fatty acid esters (e.g., isopropyl myristate), vegetable oils, mineral oils, or combinations thereof), by weight of the composition, for example, less than 5% by weight or less than 3% by weight or less than 1% by weight, of such hydrophobic liquids.

1.26 Any foregoing composition, wherein the composition is free or substantially free of any hydrophobic liquid or mixture of hydrophobic liquids (e.g., less than 0.1% by weight of the composition).

1.27 Any of Compositions 1 or 1.1-1.24, wherein the composition comprises at least 10% of any hydrophobic liquid or mixture of hydrophobic liquids (e.g., alkyl fatty acid esters (e.g., isopropyl myristate), vegetable oils, mineral oils, or combinations thereof), by weight of the composition, for example, 10-90% by weight, or 20-80% by weight, or 30-70% by weight, or 30-50% by weight, or 10-50% by weight, or 10-30% by weight, of such hydrophobic liquids.

1.28 Any foregoing composition, further comprising a nonionic surfactant, e.g., a hydrophilic nonionic surfactant.

1.29 Composition 1.28, wherein the nonionic surfactant is a copolymer of ethylene oxide and propylene oxide, for example, a block copolymer (e.g., a triblock copolymer).

1.30 Composition 1.29, wherein the nonionic surfactant is a poloxamer, e.g., a triblock copolymer having a hydrophobic polypropylene glycol block flanked by hydrophilic polyethylene glycol blocks.

1.31 Composition 1.30, wherein the poloxamer has a polyethylene glycol block length of about 75 to 125 units (e.g., about 100-101), and a polypropylene block length of about 25 to 75 units (e.g., about 55-56), for example, poloxamer 407 or Pluronic F127.

1.32 Any foregoing composition, comprising a nonionic surfactant in an amount of 0.01 to 5.0%, by weight of the composition, e.g., 0.1 to 1.0%, 0.2 to 0.7%, 0.3 to 0.5%, about 0.4%.

1.33 Any foregoing composition, further comprising an anionic surfactant, e.g., selected from sodium laurel ether sulfate (SLES), sodium lauryl sulfate, and ammonium lauryl sulfate.

1.34 Any foregoing composition wherein the composition further comprises one or more of a thickener (e.g., xanthan gum or carboxymethyl cellulose, such as sodium salt), a buffer, a sweetener, a flavorant, a pigment, a dye, an anti-caries agent, an anti-bacterial agent, a whitening agent, a desensitizing agent, a preservative, or a mixture thereof.

1.35 Any foregoing composition wherein the composition further comprises an additional fluoride ion source.

1.36 Composition 1.35, wherein the additional fluoride ion source is selected from sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, or a mixture thereof.

1.37 Any foregoing composition wherein the composition comprises a whitening agent.

1.38 Any foregoing composition wherein the composition comprises a whitening agent, wherein the whitening agent is hydrogen peroxide.

1.39 Any foregoing composition wherein the composition further comprises a desensitizing agent selected from potassium chloride, strontium chloride, or a mixture thereof.

1.40 Any foregoing composition wherein the composition is a mouthwash.

1.41 Any foregoing composition wherein the composition is a dentifrice (e.g., a toothpaste or a tooth gel).

1.42 Any foregoing composition, wherein the composition is free of abrasives (e.g., the composition is free of silicas).

1.43 Any foregoing composition, wherein the composition comprises abrasive (e.g. silicas) in an amount of 1-30% by weight of the composition, e.g., 10-30%, or 20-25%, or 15-20%.

1.44 Any of the foregoing compositions, wherein the composition is effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing and/or malodor producing bacteria, (viii) treat, relieve or reduce dry mouth, (ix) clean the teeth and oral cavity, (x) whiten the teeth, (xi) reduce tartar build-up, (xii) reduce or prevent oral malodor, and/or (xiii) promote systemic health, including cardiovascular health, e.g., by reducing potential for systemic infection via the oral tissues.

1.45 Any foregoing composition, wherein the composition has enhanced stannous ion stability (e.g., compared to a composition comprising stannous fluoride or stannous chloride without both a nitrate ion source and a polyphosphate).

1.46 Any foregoing composition, wherein the composition is packaged in a container comprising a single storage compartment, which compartment comprises the composition, and a closure (e.g., a screw-top closure) which seals the compartment.

1.47 Any foregoing composition further comprising one or more of a zwitterionic surfactant (e.g., betaine), and a nonionic polymer (e.g., a polyethylene glycol, such as PEG-600).

1.48 Any foregoing composition, wherein the composition has less than 20% by weight of any one polymeric thickener (e.g., xanthan gum, carrageenan gum, carboxymethyl cellulose, such as sodium CMC), such as less than 15% by weight, or less than 10% by weight, or less than 5% by weight, or less than 1% by weight, or 0.05-1%, or 0.05-0.5%, or 0.25 to 0.75%, by weight, or about 0.5% by weight.

1.49 Any foregoing composition, wherein the composition has less than 40% by weight of any silica (e.g., thickening silica), such as 10-40%, or 10-30%, or 10-20% or 0-20%, or 0-10%, or about 15% by weight.

1.50 Any foregoing composition, wherein the composition is substantially transparent, e.g., having a % transmittance of visible light of 10-90% for a sample thickness of 20-25 mm (e.g., 15-50%), or >30-90% for a sample thickness of 15-20 mm, or 50-90% for a sample thickness of 10-15 mm, or 70-100% for a sample thickness of 5-10 mm.

1.51 Any foregoing composition, in the form of a gel having cylindrical cross section (e.g., diameter of 5-15 mm or 8-10 mm).

1.52 Any foregoing composition, in the form of a gel having a flat ribbon cross-section (e.g. with a thickness of 2-15 mm 5-10 mm).

In a second aspect, the present disclosure further provides a method (Method 1) of stabilizing stannous ion in an aqueous oral care composition comprising the steps of (1) providing an aqueous vehicle, (2) adding to the aqueous vehicle a stannous ion source, (3) adding to the aqueous vehicle a nitrate ion source, and (4) adding to the aqueous vehicle a polyphosphate ion source, wherein the final composition is a single-component high-water composition (e.g., at least 10% water).

For example, the disclosure provides embodiments of Method 1 as follows:

1.1 Method 1, wherein the stannous ion source is a water-soluble stannous salt.

1.2 Method 1 or 1.1, wherein the stannous salt is selected from stannous chloride and stannous fluoride.

1.3 Method 1.2, wherein the stannous salt is stannous fluoride.

1.4 Any preceding method, wherein the nitrate ion source is nitric acid or a water-soluble nitrate salt.

1.5 Method 1.4, wherein the water-soluble nitrate salt is selected from an alkali or alkaline earth metal nitrate, or zinc nitrate, silver nitrate, or ammonium nitrate.

1.6 Method 1.4, wherein the water-soluble nitrate salt is an alkali metal nitrate salt or an alkaline earth metal nitrate salt.

1.7 Method 1.6, wherein the nitrate salt is selected from lithium nitrate, sodium nitrate, potassium nitrate, magnesium nitrate, and calcium nitrate.

1.8 Method 1.7, wherein the nitrate salt is potassium nitrate.

1.9 Any preceding method, wherein the polyphosphate ion source is a water-soluble alkali metal polyphosphate.

1.10 Method 1.9, wherein the water-soluble alkali metal polyphosphate is selected from a pyrophosphate, tripolyphosphate, tetraphosphate or hexametaphosphate.

1.11 Method 1.10, wherein the water-soluble alkali metal polyphosphate is a sodium or potassium polyphosphate.

1.12 Method 1.11, wherein the water-soluble alkali metal polyphosphate is selected from sodium pyrophosphate, potassium pyrophosphate, sodium tripolyphosphate and potassium tripolyphosphate.

1.13 Method 1.12, wherein the sodium pyrophosphate salt is selected from sodium acid pyrophosphate (i.e., disodium pyrophosphate) and tetrasodium pyrophosphate.

1.14 Any preceding method, wherein the stannous salt is stannous fluoride, the nitrate salt is potassium nitrate, and the polyphosphate salt is tetrasodium pyrophosphate.

1.15 Any preceding method, wherein the composition is formulated to have a molar ratio of polyphosphate source (e.g., tetrasodium pyrophosphate or sodium tripolyphosphate) to stannous source (e.g., stannous fluoride) of at least 1:1, e.g., 1:1 to 5:1, or 1:1 to 4:1, or 1:1 to 3:1, or 1:1 to 2:1, or 1.5:1 to 5:1, or 2:1 to 5:1, or 2:1 to 4:1, or 2:1 to 3:1, or about 1:1.

1.16 Any preceding method, wherein the composition is formulated to have a molar ratio of nitric acid or nitrate source (e.g., potassium nitrate) to stannous source (e.g., stannous fluoride) of at least 0.3:1, e.g., 0.3:1 to 20:1, or 0.5:1 to 20:1, or 1:1 to 20:1, or 1:1 to 15:1, or 1:1 to 10:1, or 1:1 to 5:1 or 1:1 to 3:1, or about 1:1.

1.17 Any preceding method, wherein the composition is formulated to comprise from 0.1 to 2% stannous ion source (e.g., stannous fluoride), by weight of the composition, e.g., 0.1 to 1%, or 0.25 to 0.75%, or about 0.45%.

1.18 Any preceding method, wherein the composition is formulated to comprise from 0.1 to 5% of nitric acid or nitrate ion source (e.g., potassium nitrate), by weight of the composition, e.g., 0.1 to 2%, or 0.1 to 1%, or 0.1 to 0.5%, or 0.2 to 0.4%, or 0.25 to 0.75%, about 0.3%, or about 0.5%.

1.19 Any preceding method, wherein the composition is formulated to comprise from 0.1 to 5% of polyphosphate ion source (e.g., tetrasodium pyrophosphate), by weight of the composition, e.g., 0.8 to 5%, or 0.8 to 4%, or 0.8 to 3%, or 0.8 to 2%, or 0.8 to 1.0%, or 1.0 to 1.5%, or about 0.8%, or about 1.2%.

1.20 Any preceding method, wherein the aqueous vehicle comprises water and optionally one or more humectants (e.g., glycerin, sorbitol, propylene glycol, or a mixture thereof).

1.21 Any preceding method, wherein the composition is formulated to comprise from 10 to 95% water, by weight of the composition, e.g., from 20 to 95%, or from 30 to 95%, or from 40 to 95%, or from 50 to 95%, or from 60 to 95% or from 65 to 95%, by weight of the composition, or about 20%, or about 40%, or about 60% or about 80%.

1.22 Any preceding method, wherein the composition is formulated to comprise 70% to 95% water, by weight of the composition, e.g., from 75% to 95%, or from 75% to 90%, or from 75% to 85%, or from 75% to 80%; or wherein the composition is formulated to comprise from 10% to 50% water, by weight of the composition, e.g., 10% to 40%, or 10% to 30%, or about 20%.

1.23 Any preceding method, wherein the composition is formulated to comprise one or more humectants (e.g., glycerin, sorbitol, propylene glycol, or a mixture thereof) in a net amount of 5 to 75% by weight of the composition, e.g., from 5% to 25% by weight of the composition, or from 10% to 25%, or from 15% to 25%, or about 20%, or from 30 to 70%, or from 35 to 60%, or from 40 to 60%, or from 60 to 70%, by weight of the composition.

1.24 Any preceding method, wherein the composition is formulated as a single phase, i.e., it does not form two phases on standing.

1.25 Any preceding method, wherein the composition is formulated as a clear (e.g., not opaque or turbid) solution (e.g., not a suspension) or a clear (e.g., translucent, not opaque) semisolid or gel.

1.26 Any preceding method, wherein the composition is physically and chemically stable, for example, wherein no color change or precipitation occurs on storage at ambient conditions for 3 months or more (e.g., 6 months or more, or 1 year or more).

1.27 Method 1.27, wherein the stannous ion concentration is substantially stable for at least three months on storage, e.g., the concentration of stannous ion is at least 80% of the original concentration, or at least 85%, or at least 90%.

1.28 Any preceding method, wherein the composition has a pH of between 5 and 9, or a pH between 6 and 8, or a pH between 6.5 and 7.5, or a pH between 6.9 and 7.1, or a pH of about 7.

1.29 Any preceding method, wherein the composition is formulated to comprise less than 10% of any hydrophobic liquid or mixture of hydrophobic liquids (e.g., alkyl fatty acid esters (e.g., isopropyl myristate), vegetable oils, mineral oils, or combinations thereof), by weight of the composition, for example, less than 5% by weight or less than 3% by weight or less than 1% by weight, of such hydrophobic liquids.

1.30 Any preceding method, wherein the composition is formulated to be free or substantially free of any hydrophobic liquid or mixture of hydrophobic liquids (e.g., less than 0.1% by weight of the composition), i.e., the method does not comprise any step of adding any hydrophobic liquid to the aqueous vehicle.

1.31 Any preceding method, wherein the composition is formulated to comprise a nonionic surfactant, e.g., a hydrophilic nonionic surfactant, i.e., the method further comprises the step (5) of adding a nonionic surfactant to the aqueous vehicle.

1.32 Method 1.31, wherein the nonionic surfactant is a copolymer of ethylene oxide and propylene oxide, for example, a block copolymer (e.g., a triblock copolymer).

1.33 Method 1.31, wherein the nonionic surfactant is a poloxamer, e.g., a triblock copolymer having a hydrophobic polypropylene glycol block flanked by hydrophilic polyethylene glycol blocks.

1.34 Method 1.33, wherein the poloxamer has a polyethylene glycol block length of about 75 to 125 units (e.g., about 100-101), and a polypropylene block length of about 25 to 75 units (e.g., about 55-56), for example, poloxamer 407 or Pluronic F127.

1.35 Any of methods 1.31-1.34, wherein the composition is formulated to comprise the nonionic surfactant in an amount of 0.01 to 5.0%, by weight of the composition, e.g., 0.1 to 1.0%, 0.2 to 0.7%, 0.3 to 0.5%, about 0.4%

1.36 Any preceding method, wherein the composition is a mouthwash.

1.37 Any preceding method, wherein the composition is a dentifrice (e.g., a toothpaste or a tooth gel).

1.38 Any preceding method, wherein the composition is formulated to comprise abrasive (e.g. silicas) in an amount of 1-30% by weight of the composition, e.g., 10-30%, or 20-25%.

1.39 Any preceding method, wherein the composition is formulated to be free of abrasives (e.g., the composition is formulated to be free of silicas).

1.40 Any preceding method, wherein step (1) occurs first and steps (2)-(5) occur in any order.

1.41 Any preceding method, further comprising a final step (6) of packaging the composition in a container comprising a single storage compartment, which compartment comprises the composition, and a closure (e.g., a screw-top closure) which seals the compartment.

1.42 Any preceding method, wherein the method results in a composition according to Composition 1, or any of 1.1-1.52.

In a third aspect, the present disclosure provides an oral care package comprising a composition according to Composition 1, or any of 1.1-1.52, wherein the package comprises a container comprising a single storage compartment, which compartment contains the composition, and a closure (e.g., a screw-top closure) which seals the compartment. In some embodiments, wherein the composition is a toothpaste or gel, the package comprises a closure which dispenses a ribbon of toothpaste or gel having a circular cross-section, oval cross-section, or flat-ribbon cross-section. In some embodiments, such ribbon is dispensed having a diameter or thickness of 5-25 mm, e.g., 5-10 mm, or 10-15 mm, or 15-20 mm, or 20-25 mm.

In a fourth aspect, the present disclosure provides a method of treatment or prevention of gingivitis, plaque, dental caries, and/or dental hypersensitivity, the method comprising the application to the oral cavity of a person in need thereof, of a composition according to the invention (e.g., Composition 1 et seq.), e.g., by brushing, for example, one or more times per day.

Alternatively, the present disclosure provides Composition 1, et seq., for use in the treatment or prevention of gingivitis, plaque, dental caries, and/or dental hypersensitivity.

The methods of the fourth aspect comprise applying any of the compositions as described herein to the teeth, e.g., by brushing, gargling or rinsing, or otherwise administering the compositions to the oral cavity of a subject in need thereof. The compositions can be administered regularly, such as, for example, one or more times per day (e.g., twice per day). In various embodiments, administering the compositions of the present disclosure to teeth may provide one or more of the following specific benefits: (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing and/or malodor producing bacteria, (viii) treat, relieve or reduce dry mouth, (ix) clean the teeth and oral cavity, (x) whiten the teeth, (xi) reduce tartar build-up, (xii) reduce or prevent oral malodor, and/or (xiii) promote systemic health, including cardiovascular health, e.g., by reducing potential for systemic infection via the oral tissues.

As used herein, an "oral care composition" refers to a composition for which the intended use includes oral care, oral hygiene, and/or oral appearance, or for which the intended method of use comprises administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "single component" means an oral care composition comprising at most a single compositional component at any time. Thus, this is in distinction to a "dual-component" compositions, which is manufactured as two separate compositions, maintained separately until final point of use. For example, a dual component toothpaste is typically packaged in a tube containing two parallel compartments exiting via a common nozzle such that when the user extrudes the toothpaste from the package the two components mix immediately prior to application to the oral cavity. Likewise, a dual component mouthwash is typically packaged in a bottle comprising two compartments such that a measured amount of the liquid from each compartment is dispensed and mixed when the user. Dual component compositions are often used to maintain in separate components and compartments ingredients which are mutually incompatible, such that if kept in the same component they would adversely react or interfere with each other.

In contrast, a dual-phase composition, such as a mouthwash, is a single-component composition comprising two immiscible liquids which settle into two phases on standing. Such a composition has no need for separated compartments for storage because the natural tendency of the two phases to separate helps ensure that the ingredients in one phase are not maintained in intimate contact with the ingredients of the other phase. Nevertheless, when vigorously mixed, the two phases become intimately combined (such as, to form an emulsion), which may or may not separate back into the two phases on standing.

As used herein, "anionic surfactant" means those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen. Some examples of suitable anionic surfactants include, but are not limited to, the sodium, potassium, ammonium, and ethanolammonium salts of linear $C_8$-$C_{18}$ alkyl ether sulfates, ether sulfates, and salts thereof. Suitable anionic ether sulfates have the formula $R(OC_2H_4)_n OSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (SLES), sodium lauryl sulfate, and ammonium lauryl sulfate. In certain embodiments, the anionic surfactant is present in an amount of 0.01 to 5.0%, 0.1 to 2.0%, 0.2 to 0.4%, or about 0.33%.

As used herein, "nonionic surfactant" generally refers to compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coco ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

In some embodiments, the nonionic surfactant comprises amine oxides, fatty acid amides, ethoxylated fatty alcohols, block copolymers of polyethylene glycol and polypropylene glycol, glycerol alkyl esters, polyoxyethytene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonoethanolamide, lauramide monoethanolamide, cocodiethanolamide, and mixtures thereof. In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonoethanolamide. In certain embodiments, the nonionic surfactant is present in an amount of 0.01 to 5.0%, 0.1 to 2.0%, 0.1 to 0.6%, 0.2 to 0.4%, about 0.2%, or about 0.5%.

Mouthwashes frequently contain significant levels of ethanol, which is often needed to solubilize essential oils and to prevent bacterial contamination. High levels of ethanol may be undesirable, because in addition to the potential for abuse by ingestion, the ethanol may exacerbate conditions like xerostomia. Accordingly, in some embodiments, the oral care compositions of the invention are substantially free of ethanol, e.g., contain less than 1% ethanol.

Humectants can enhance the viscosity, mouthfeel, and sweetness of the product, and may also help preserve the product from degradation or microbial contamination. Suitable humectants include edible polyhydric alcohols such as glycerin, sorbitol, xylitol, propylene glycol as well as other polyols and mixtures of these humectants. Sorbitol may in some cases be provided as a hydrogenated starch hydrolysate in syrup form, which comprises primarily sorbitol (the product if the starch were completely hydrolyzed to glucose, then hydrogenated), but due to incomplete hydrolysis and/or presence of saccharides other than glucose, may also include other sugar alcohols such mannitol, maltitol, and longer chain hydrogenated saccharides, and these other sugar alcohols also function as humectants in this case. In some embodiments, humectants are present at levels of 5% to 25%, e.g., 15% to 20% by weight.

Flavorings for use in the present invention may include extracts or oils from flavorful plants such as peppermint, spearmint, cinnamon, wintergreen, and combinations thereof, cooling agents such as menthol, methyl salicylate, and commercially available products such as OptaCool® from Symrise, as well as sweeteners, which may include polyols (which also function as humectants), saccharin, acesulfame, aspartame, neotame, stevia and sucralose.

Other ingredients which may optionally be included in compositions according to the present invention include hyaluronic acid, green tea, ginger, sea salt, coconut oil, turmeric, white turmeric (white curcumin), grape seed oil, ginseng, monk fruit, vitamin E, basil, chamomile, pomegranate, aloe vera, and charcoal. Any of such ingredients may be present in an amount from 0.01% to 2% by weight of the composition, e.g., 0.01 to 1%, or 0.01 to 0.5%, or 0.01 to 0.1%.

EXAMPLES

Unless otherwise noted, the pH of all solutions described in the Examples is about 7. Unless otherwise noted, all FIGURES for stannous ion concentration refer to soluble stannous, not total stannous (total stannous being soluble and insoluble stannous combined).

Example 1—Stabilization of Stannous Fluoride in Aqueous Solution by Potassium Nitrate and Tetrasodium Pyrophosphate Simple solutions of 0.454% stannous fluoride in water combined with different stabilizing agents are compared using visual observation and assays for soluble stannous ion concentration. As a baseline, a solution of 0.454% stannous fluoride in water is compared to a solution of 0.454% stannous fluoride and 5.0% potassium nitrate. Both solutions have a pH of 7. The solutions are aged at room temperature for 30 days, and soluble stannous ion content is measured at 1 day, 5 days, 9 days, 15 days, and 26 days. Stannous ion (Sn(II)) concentration is determined by titration. 0.1 N iodine solution is first added to a sample of the solution and stirred for at least one hour. The solution is observed to turn brown. 0.1 N sodium thiosulfate solution is then added until the mixture turns and remains stably white. The amount of soluble stannous ion is then calculated as the difference between the molar amount of iodine added and the molar amount of sodium thiosulfate added, and this molar amount of soluble stannous ion is converted to a concentration FIGURE. The concentration value so determined is then converted to a percentage of the theoretical amount of stannous(II) which should be present based on the formulation of the solution.

The results are shown in the table below, expressed as the percentage of soluble stannous compared to the theoretical amount:

|  | Day 1 | Day 5 | Day 9 | Day 15 | Day 26 |
|---|---|---|---|---|---|
| $SnF_2$ | 96% | 93% | 89% | 80% | 63% |
| $SnF_2$ + $KNO_3$ | 100% | 100% | 94% | 83% | 68% |

The results show that at neutral pH, potassium nitrate by itself improves stannous ion stability initially, but by day 9, stannous ion concentration continues to fall comparable to the unstabilized stannous fluoride solution. It is also observed that both solutions are initially turbid, and continued aging results in the solutions becoming yellow and remaining turbid. For comparison, a solution of $SnF_2$ at its native pH (acidic) is clear and colorless and remains so through aging. Thus, this demonstrates that a solution of stannous ion at near or above neutral pH is unstable, but that potassium nitrate provides short-lived stabilization.

In a second set of experiments, the stability of 0.454% stannous fluoride is compared in solutions which each comprise 0.3% potassium nitrate and optionally a second chelating agent. The second agent is selected from 0.77% tetrasodium pyrophosphate (TSPP), 2.2% sodium citrate, 1.0% sodium gluconate, and 0.5% arginine, and the resulting three-component solutions have a pH of 7 in each case. Each solution is clear, colorless and homogenous, except for the solution with arginine, which is initially turbid. 0.454% stannous fluoride in water is included as a negative control. As a positive control, one solution consists of 0.454% stannous fluoride and 0.3% potassium nitrate acidified to pH 3. As noted previously, it has been reported that at a pH below 6, potassium nitrate alone stabilizes stannous fluoride in solution, and that result is confirmed here. In this experiment, aging is conducted at 60° C. with stannous ion concentration measured at 0 days, 6 or 7 days and at 14 days. The results are shown in the table below, expressed as the percentage of soluble stannous compared to the theoretical amount:

|  | Day 0 | Day 6 | Day 7 | Day 14 |
|---|---|---|---|---|
| $SnF_2$ + $KNO_3$ + TSPP | 100% | 96% |  | 87% |
| $SnF_2$ + $KNO_3$, pH 3 | 98% |  | 92% | 85% |
| $SnF_2$ + $KNO_3$ + citrate | 99% | 81% |  | 55% |

-continued

|  | Day 0 | Day 6 | Day 7 | Day 14 |
|---|---|---|---|---|
| $SnF_2$ + $KNO_3$, + gluconate | 100% | 47% |  | 44% |
| $SnF_2$ + $KNO_3$ + arginine | 100% | 29% |  | 17% |
| $SnF_2$ | 99% |  | 32% | 7% |

It is found that the stannous fluoride/potassium nitrate/TSPP solution remains homogenous at day 14, showing no signs of insoluble tin precipitation. The data demonstrates that absent a stabilizing agent, less than 10% of the original stannous ion remains available in solution after 14 days at 60° C. Potassium nitrate effectively stabilizes stannous ion under these conditions at a pH of 3, but not at neutral pH, as seen by comparing these results with the preceding results. Unexpectedly, however, the combination of potassium nitrate and TSPP at neutral pH stabilizes stannous as effectively as potassium nitrate alone at acidic pH. The same effect is not obtained using alternative chelating agents, such as citrate, gluconate and arginine. Thus, the particular combination of potassium nitrate and TSPP is shown to provide a synergistic stabilizing effect on stannous ion.

While potassium nitrate is found to stabilize stannous ion at acidic pH, it is also found that the solution undergoes an undesirable discoloration at the same time. This is most apparent after 4 weeks of aging at 60° C. While the stannous fluoride/potassium nitrate/TSPP solution remains homogenous and colorless after 4 weeks, the stannous fluoride/potassium nitrate/pH 3 solution becomes clearly yellow. This is confirmed by comparing UV/Vis spectroscopy, which shows a peak at about 300-310 nm wavelength in the acidic solution, which is not present in the neutral solution with TSPP.

In a third experiment, the effect of sodium tripolyphosphate (STPP) is compared to the effect of TSPP in stabilizing stannous over 2 weeks of aging at 60° C. It is found that STPP provides comparable benefits to TSPP, and these are both demonstrated as being synergistic effects resulting from the interaction of the potassium nitrate and the polyphosphate salt. The results are shown in the table below:

| Components (wt %) | | | | % Stannous, |
|---|---|---|---|---|
| $SnF_2$ | $KNO_3$ | TSPP | STPP | Day 14 |
| 0.454 | 0 | 0 | 0 | 7.5% |
| 0.454 | 0.3 | 0 | 0 | 9.0% |
| 0.454 | 0 | 0.77 | 0 | 37% |
| 0.454 | 0 | 0 | 1.07 | 32% |
| 0.454 | 0.3 | 0.77 | 0 | 87% |
| 0.454 | 0.3 | 0 | 1.07 | 93% |

Example 2: Stability of Stannous Fluoride/Potassium Nitrate/TSPP Mixture Over a Range of Ratios A series of comparative solutions comprising stannous fluoride, potassium nitrate and TSPP are prepared and subjected to aging for 14 days at 60° C. On day 14, soluble stannous ion concentration is measured and visual observations are made. All solutions have 0.454% stannous fluoride, and the amounts of potassium nitrate and TSPP are adjusted to arrive at the desired molar ratios. The results are shown in the table below:

| Molar Ratio | | | % Stannous, |
|---|---|---|---|
| $SnF_2$ | $KNO_3$ | TSPP | Day 14 |
| 1 | 1 | 0 | 9% |
| 1 | 1 | 0.07 | 29% (turbid) |
| 1 | 1 | 0.1 | 25% (turbid) |
| 1 | 1 | 0.3 | 83% (turbid) |
| 1 | 1 | 0.7 | 83% (turbid) |
| 1 | 1 | 1 | 87% |
| 1 | 1 | 1.3 | 87% |
| 1 | 1 | 2 | 78% |
| 1 | 1 | 2.6 | 73% |
| 1 | 1 | 5.2 | 59% |
| 1 | 0 | 1 | 37% |
| 1 | 0.04 | 1 | 52% |
| 1 | 0.1 | 1 | 73% |
| 1 | 0.2 | 1 | 75% |
| 1 | 0.3 | 1 | 80% |
| 1 | 0.7 | 1 | 86% |
| 1 | 1 | 1 | 87% |
| 1 | 2 | 1 | 86% |
| 1 | 3.4 | 1 | 88% |
| 1 | 7 | 1 | 85% |
| 1 | 12 | 1 | 83% |
| 1 | 17 | 1 | 84% |
| 1 | 34 | 1 | 76% |

It is found that at a molar ratio of 1:1 stannous fluoride to potassium nitrate, a high level of stannous ion stability (>80%) and solution homogeneity can be obtained over a stannous fluoride to TSPP molar ratio of 1:1 to 1:2.5. When less TSPP is used, a precipitate forms even while maintaining acceptable stannous ion stability, while when the lowest or highest amounts of TSPP are employed, stannous ion stability drops.

It is further found that at a molar ratio of 1:1 stannous fluoride to TSPP, a high level of stannous ion stability (>80%) and solution homogeneity can be obtained over a wide range of stannous fluoride/potassium nitrate molar ratios.

Together these results further support the unique unexpected synergy between potassium nitrate and TSPP ins stabilizing stannous ion in aqueous solution.

Example 3—Stability of Stannous Fluoride/Potassium Nitrate/STPP Mixture Over a Range of Ratios To evaluate whether the same stabilization effect can be obtained using a tripolyphosphate salt, the same experimental procedure as outlined in Example 2 was repeated using sodium tripolyphosphate instead of tetrasodium pyrophosphate. The results are shown in the table below.

| Molar Ratio | | | % Stannous, |
|---|---|---|---|
| $SnF_2$ | $KNO_3$ | TSPP | Day 14 |
| 1 | 1 | 0 | 9% |
| 1 | 1 | 0.05 | 69% (turbid) |
| 1 | 1 | 0.1 | 84% (turbid) |
| 1 | 1 | 0.3 | 86% (turbid) |
| 1 | 1 | 0.5 | 90% (turbid) |

-continued

| Molar Ratio | | | % Stannous, |
|---|---|---|---|
| $SnF_2$ | $KNO_3$ | TSPP | Day 14 |
| 1 | 1 | 0.7 | 91% (turbid) |
| 1 | 1 | 1 | 92% |
| 1 | 1 | 1.5 | 92% |
| 1 | 1 | 2 | 87% |
| 1 | 1 | 3 | 87% |
| 1 | 1 | 4 | 83% |
| 1 | 1 | 6 | 82% |
| 1 | 1 | 8 | 79% |
| 1 | 1 | 10 | 79% |
| 1 | 0 | 1 | 32% |
| 1 | 0.03 | 1 | 74% |
| 1 | 0.1 | 1 | 84% |
| 1 | 0.2 | 1 | 86% |
| 1 | 0.3 | 1 | 91% |
| 1 | 1 | 1 | 93% |
| 1 | 2 | 1 | 95% |
| 1 | 3.4 | 1 | 96% |
| 1 | 7 | 1 | 95% |
| 1 | 17 | 1.5 | 92% |
| 1 | 34 | 1.5 | 86% |

As found with TSPP, the combination of STPP and potassium nitrate is found to result in stabilization of stannous over wide concentration ranges and ratios. It is further found that high stannous stability can be achieved using lower concentrations of STPP than for TSPP.

Example 4—Additional Studies on Stannous/Nitrate/Phosphate Systems

Additional studies are performed using the same 14-day, 60° C. accelerated aging study design, in which variations are made in the concentrations and/or components of the tested solutions.

In one experiment, the stabilizing effect of potassium nitrate and TSPP or STPP on stannous chloride is compared to the effect on stannous fluoride. As shown in the table below, it is found that STPP is somewhat more effective in stabilizing stannous chloride than TSPP is, although both polyphosphates provide effective stabilization of both stannous salts.

| Components (wt %) | | | | | % Stannous, |
|---|---|---|---|---|---|
| $SnF_2$ | $SnCl_2$ | $KNO_3$ | TSPP | STPP | Day 14 |
| 0.454 | 0 | 0.3 | 0.77 | 0 | 87% |
| 0 | 0.64 | 0.3 | 0.77 | 0 | 79% |
| 0.454 | 0 | 0.3 | 0 | 1.07 | 93% |
| 0 | 0.64 | 0.3 | 0 | 1.07 | 93% |

In another experiment, sodium nitrate or potassium chloride are compared to potassium nitrate in order to further evaluate the role of potassium nitrate in stabilizing stannous. The results are shown in the table below. It is found that sodium nitrate provides a comparable stabilizing affect as potassium nitrate, whereas potassium chloride does not provide an additive stabilizing effect. The stannous stability obtained in an $SnF_2$/KCl/TSPP or $SnF_2$/KCl/STPP system is comparable to the results obtained above for an $SnF_2$/TSPP or $SnF_2$/STPP system, as shown in Example 1 (32% stannous at day 14 using STPP, and 37% using TSPP). Thus, it is apparent that the nitrate anion provides a unique stabilizing effect which is not obtained using the isoelectronic and comparably sized chloride anion. Moreover, it is seen that the choice of cation to the nitrate anion makes a negligible difference to the outcome.

| Components (wt %) | | | | | | % Stannous, |
|---|---|---|---|---|---|---|
| $SnF_2$ | $KNO_3$ | $NaNO_3$ | KCl | TSPP | STPP | Day 14 |
| 0.454 | 0.3 | 0 | 0 | 0.77 | 0 | 87% |
| 0.454 | 0 | 0.25 | 0 | 0.77 | 0 | 86% |
| 0.454 | 0 | 0 | 0.23 | 0.77 | 0 | 34% |
| 0.454 | 0.6 | 0 | 0 | 0 | 1.6 | 96% |
| 0.454 | 0 | 0.5 | 0 | 0 | 1.6 | 94% |
| 0.454 | 0 | 0 | 0.46 | 0 | 1.6 | 40% |

In another experiment, the initial concentration of stannous fluoride is varied to determine the range over which the $KNO_3$/polyphosphate system provides a stabilizing effect. Two stabilizing systems are evaluated: $SnF_2$/$KNO_3$/TSPP at a 1:1:1 molar ratio, and $SnF_2$/$KN_2$/STPP at a 1:2:1 molar ratio. The results are shown in the table below. It is unexpectedly found that the $KNO_3$/TSPP system provides highly effective stabilizing over an initial stannous fluoride concentration range of 0.1 to 1.7%, but this efficiency drops at lower initial stannous fluoride concentrations. In contrast, the $KNO_3$/STPP system provides effective stabilization over the entire stannous fluoride concentration range tested.

| Components (wt %) | | | | % Stannous, |
|---|---|---|---|---|
| $SnF_2$ | $KNO_3$ | TSPP | STPP | Day 14 |
| 0.05 | 0.03 | 0.077 | 0 | 2% |
| 0.09 | 0.06 | 0.16 | 0 | 52% |
| 0.15 | 0.1 | 0.27 | 0 | 73% |
| 0.20 | 0.13 | 0.36 | 0 | 80% |
| 0.45 | 0.3 | 0.77 | 0 | 87% |
| 1.0 | 0.66 | 1.7 | 0 | 91% |
| 2.0 | 1.3 | 4.4 | 0 | 90% |
| 2.5 | 1.7 | 5.6 | 0 | 91% |
| 0.05 | 0.06 | 0 | 0.11 | 77% |
| 0.07 | 0.09 | 0 | 0.18 | 86% |
| 0.09 | 0.12 | 0 | 0.22 | 91% |
| 0.15 | 0.19 | 0 | 0.37 | 92% |
| 0.45 | 0.6 | 0 | 1.1 | 95% |
| 1.0 | 1.3 | 0 | 2.4 | 91% |
| 1.7 | 2.2 | 0 | 6.0 | 86% |

In an additional experiment, the stannous chloride/potassium nitrate/TSPP (1:1 stannous to nitrate, 1:1 or 1:1.5 stannous to TSPP) and the stannous chloride/potassium nitrate/STPP (1:2 stannous to nitrate, 1:1, 1:1.5 or 1:3 stannous to STPP) systems are evaluated at a different pH values. In order to achieve an initially clear, homogenous solution, a higher concentration of the polyphosphate is required at higher pH values (pH 8 or 9). At pH 9, the STPP-based system (1:2:3 molar ratio) is initially slightly turbid, but it becomes clear prior to the end of the study. It is unexpectedly found that the STPP-based system provides improved stabilization over the somewhat broader pH range compared to the TSPP-based system. The results are shown in the table below:

| Components (wt %) | | | | | % Stannous, |
|---|---|---|---|---|---|
| $SnF_2$ | $KNO_3$ | TSPP | STPP | pH | Day 14 |
| 0.454 | 0.3 | 0.77 | 0 | 6 | 84% |
| 0.454 | 0.3 | 0.77 | 0 | 7 | 87% |

-continued

| Components (wt %) | | | | | % Stannous, |
|---|---|---|---|---|---|
| SnF$_2$ | KNO$_3$ | TSPP | STPP | pH | Day 14 |
| 0.454 | 0.3 | 1.2 | 0 | 8 | 68% |
| 0.454 | 0.6 | 0 | 1.07 | 6 | 95% |
| 0.454 | 0.6 | 0 | 1.07 | 7 | 95% |
| 0.454 | 0.6 | 0 | 1.6 | 8 | 94% |
| 0.454 | 0.6 | 0 | 3.2 | 9 | 76% |

Example 5—Mouthwash Formulations

Exemplary mouthwash compositions according to the present disclosure may be formulated as follows (quantities shown in % by weight of the composition):

| | Example number | | | |
|---|---|---|---|---|
| | A | B | C | D |
| Stannous Ion Concentration (ppm) | 680 | 3400 | 340 | 340 |
| SnF$_2$:KNO$_3$:TSPP molar ratio | 1:1:1 | 1:1:1 | 1:1:1 | 1:4:1 |
| Water | Q.S. (~79) | Q.S. (~78) | Q.S. (~79) | Q.S. (~79) |
| Nonionic surfactant (e.g., Poloxamer 407) | 0.4 | 0.4 | 0.4 | 0.4 |
| Stannous Fluoride | 0.09 | 0.454 | 0.0454 | 0.0454 |
| Potassium Nitrate | 0.059 | 0.3 | 0.03 | 0.12 |
| Tetrasodium Pyrophosphate | 0.155 | 0.77 | 0.077 | 0.077 |
| Glycerin | 7.5 | 7.5 | 7.5 | 7.5 |
| Sorbitol | 5.5 | 5.5 | 5.5 | 5.5 |
| Propylene Glycol | 7 | 7 | 7 | 7 |
| Flavors, Colors, and other Minors | 0.168 | 0.168 | 0.168 | 0.168 |
| NaOH (50% Aqueous Solution)) | 0.04 | 0.06 | 0.06 | 0.06 |

These mouthwash formulations are found to be clear, colorless, homogenous solutions. The soluble stannous concentration is found to be essentially 100% of the theoretical amount.

The composition of Example A is compared to Comparative compositions E and F, which lack TSPP or potassium nitrate, respectively. The three mouthwash formulations are subjected to two weeks of aging at 60° C., after which they are assayed for soluble stannous ion, as described in Example 1. The formulations and test results are shown in the table below (quantities shown in % by weight of the composition):

| | Example number | | |
|---|---|---|---|
| | A | E | F |
| Stannous Ion Concentration (ppm) | 680 | 680 | 680 |
| SnF$_2$:KNO$_3$:TSPP molar ratio | 1:1:1 | 1:0:1 | 1:1:0 |
| Water | Q.S. (~79) | Q.S. (~79) | Q.S. (~79) |
| Nonionic surfactant (e.g., Poloxamer 407) | 0.4 | 0.4 | 0.4 |
| Stannous Fluoride | 0.09 | 0.09 | 0.09 |
| Potassium Nitrate | 0.059 | — | 0.059 |
| Tetrasodium Pyrophosphate | 0.155 | 0.155 | — |
| Glycerin | 7.5 | 7.5 | 7.5 |
| Sorbitol | 5.5 | 5.5 | 5.5 |
| Propylene Glycol | 7 | 7 | 7 |
| Flavors, Colors, and other Minors | 0.168 | 0.168 | 0.168 |
| NaOH (50% Aqueous Solution)) | 0.04 | 0.06 | 0.06 |
| pH, after 2 weeks at 60° C. | 6.45 | 5.9 | 5.6 |
| % Stannous, after 2 weeks at 60° C. | 62% | 15% | 38% |
| Appearance, after 2 weeks at 60° C. | Clear | Clear | Turbid |

It is found that the mouthwash of Example A retains substantially more stannous ion than the mouthwash of Example E and F. Further studies are repeated using mouthwashes according to Example B, and their comparative analogs (lacking potassium nitrate or TSPP). It is found that the composition of Example B results in 76% stannous concentration after 2 weeks at 60° C. After 8 weeks at 40° C., there is 85% stannous retained. These values are substantially higher than the stannous concentration obtained using the potassium nitrate-free or TSPP-free comparative compositions.

The mouthwash compositions A, E and F are further subjected to an anti-bacterial efficacy study. A commercial positive control mouthwash is included in the study (0.075% cetylpyridinium chloride, an antibacterial agent, is the active component). The commercial composition has the composition shown in the table below (quantities shown in % by weight of the composition):

| | Commercial Control |
|---|---|
| Water | Q.S. (~79) |
| Nonionic surfactant (e.g., Poloxamer 407) | 0.4 |
| Sodium saccharin | 0.02 |
| Cetylpyridinium chloride | 0.075 |
| Sodium fluoride | 0.05 |
| Glycerin | 7.5 |
| Sorbitol | 5.5 |
| Propylene Glycol | 7 |
| Potassium sorbate | 0.05 |
| Citric acid | 0.01 |
| Flavors, Colors, and other Minors | 0.166 |

The ACTA model is used to provide anti-bacterial and anti-metabolic potential efficacy of the mouthwash formulas on matured multi-species biofilms. Saliva is collected from volunteers, and this is used as inoculum for biofilm formation. Biofilm grown hydroxyapatite disks are treated with the experimental mouthwash formulas (A, E, F or the commercial control) in triplicate twice a day for the next 3 days. As a negative control (placebo) one set hydroxyapatite disks remain untreated over the 3 days.

On the fifth day, after the morning treatment, the discs are processed for recovery by placing in buffered Peptone water with sucrose for 3 hours. The recovered biofilm is assessed for bacteria using a Live/Dead Ratio assay. The Live/Dead assay is performed using Live-Dead BacLight bacterial viability kit (Life Technologies, X20454). Live-Dead reagent is prepared by adding SYTO9 and Propidium Iodide (PI) in sterile water according to the manufacturer's protocol. Harvested biofilm is added into a 96-well plate followed by the Live-Dead assay reagent and then the plate is incubated in the dark for 15 minutes. SYTO9 is read at 483 nm excitation/503 nm emission and PI is read at 535 nm excitation/615 nm emission. The ratio of Live (SYTO9) to Dead (PI) fluorescence versus treatment is plotted, and the live/dead ratio is calculated.

Freshly prepared samples of mouthwashes A, E and F are compared to the two control samples and it is found that mouthwash A has comparable anti-bacterial efficacy to the positive control, while mouthwash E and F have substantially reduced antibacterial efficacy. This is consistent with the stabilizing effect that potassium nitrate and TSPP synergistically provides on stannous ion in aqueous solution. The results of the study are shown in the table below.

| Sample | Mean Live/Dead Ratio | Statistical Grouping |
|---|---|---|
| Commercial Mouthwash | 2.61 | C |
| Mouthwash A (Fresh) | 3.26 | C |
| Mouthwash A (Aged) | 3.10 | C |
| Mouthwash E (Aged) | 4.82 | B |
| Mouthwash F (Aged) | 9.87 | A |

Example 6—Dentifrice Formulations

Exemplary dentifrice compositions according to the present disclosure may be formulated as follows (quantities shown in % by weight of the composition):

| | Example number | | | | | |
|---|---|---|---|---|---|---|
| | G Paste | H Gel | I Paste | J Paste | K Gel | L Gel |
| Stannous Ion Concentration (ppm) | 3400 | 3400 | 3400 | 3400 | 3400 | 3400 |
| $SnF_2$: $KNO_3$: TSPP/STPP molar ratio | 1:1:1 | 1:1:1 | 1:17:1.6 | 1:17:1.9 | 1:10:1.4 | 1:10:1.7 |
| Water | Q.S. (~20) | Q.S. (~12) | Q.S. (~20) | Q.S. (~20) | Q.S. (~12) | Q.S. (~12) |
| Microcrystalline cellulose (e.g., Avicel) | 1 | 0 | 1 | 1 | 0 | 0 |
| Polyethylene glycol (e.g., PEG 600) | 2 | 3 | 2 | 2 | 3 | 3 |
| Xanthan Gum | 0.3 | 0 | 0.3 | 0.3 | 0 | 0 |
| Carboxymethyl cellulose (e.g., Na CMC) | 0.8 | 0.65 | 0.8 | 0.8 | 0.8 | 0.8 |
| Stannous Fluoride | 0.454 | 0.454 | 0.454 | 0.454 | 0.454 | 0.454 |
| Potassium Nitrate | 0.3 | 0.3 | 5 | 5 | 3 | 3 |
| TSPP | 0.77 | 0.77 | 1.2 | | 1.1 | |
| STPP | | | | 2 | | 1.8 |
| Glycerin | 4 | 0 | 4 | 4 | 0 | 0 |
| Sorbitol | 44 | 55 | 39 | 38 | 52 | 52 |
| Silicas | 21.5 | 22.75 | 21.5 | 21.5 | 22.75 | 22.75 |
| Anionic surfactant (e.g., SLS) | 1.5 | 1.5 | 1.5 | 1.5 | 1.5 | 1.5 |
| Zwitterionic surfactant (e.g., betaine) | 1.25 | 1.25 | 1.25 | 1.25 | 1.25 | 1.25 |
| Flavors, Colors, and other Minors | 1.8 | 1.75 | 1.8 | 1.8 | 1.75 | 1.75 |
| NaOH (50% Aqueous Solution)) | 0.06 | 0.06 | 0 | 0 | 0 | 0 |
| Hydrochloric acid | 0 | 0 | 0.05 | 0.1 | 0 | 0.05 |

| Sample | Mean Live/Dead Ratio | Statistical Grouping |
|---|---|---|
| Commercial Mouthwash | 4.36 | C |
| Mouthwash A (Fresh) | 4.22 | C |
| Mouthwash E (Fresh) | 6.83 | B |
| Mouthwash F (Fresh) | 7.50 | B |
| Placebo | 11.50 | A |

The study is repeated after the mouthwashes A, E and F have been aged for 2 weeks at 60° C. A new fresh sample of mouthwash A is used as a positive control, in addition to the commercial mouthwash control (note that as the assay is performed using fresh inoculum, results between different assay runs are not to be compared directly). It is found that aged mouthwash A has comparable anti-bacterial efficacy to both fresh mouthwash A and the positive control, while the aged mouthwashes E and F have lost substantial efficacy. The results are shown in the table below.

Soluble stannous concentrations are determined according to the procedure described in Example 1, except that a slurry of toothpaste is first prepared in water to provide a concentration of 25 wt % toothpaste, and the 0.1 N iodine solution is added to this slurry followed by titration with sodium thiosulfate. In order to determine total stannous concentration, the slurry is formed using 2M citric acid solution instead of water (the citric acid solubilizes any insoluble stannous present). The initial soluble stannous concentration in each of these dentifrice formulations is found to be 80-94% of the theoretical amount, and the total stannous concentration in each of these formulations is found to be 90-100% of the theoretical amount.

The composition of Examples I, J, K and L are subjected to two weeks of aging at 60° C., after which they are assayed for soluble stannous ion, as described in Example 1. The test results are shown in the table below:

|  | Example number | | | |
| --- | --- | --- | --- | --- |
|  | I | J | K | L |
| SnF$_2$:KNO$_3$:TSPP/STPP molar ratio | 1:17:1.6 | 1:17:1.9 | 1:10:1.4 | 1:10:1.7 |
| Polyphosphate source | TSPP | STPP | TSPP | STPP |
| pH, after 2 weeks at 60° C. | 6.39 | 6.27 | 6.5 | 6.33 |
| % Total Stannous, after 2 weeks at 60° C. | 67% | 83% | 74% | 86% |
| % Sol. Stannous, after 2 weeks at 60° C. | 37% | 62% | 45% | 60% |

It is found that the dentifrices of Examples I to L retain a substantial portion of the initial amount of total stannous ion and soluble stannous ion, with somewhat better retention observed when the composition comprise a larger amount of the polyphosphate ion source.

Additional comparative studies are performed using comparative compositions analogous to Example I to L, except having only the potassium nitrate or only the polyphosphate source, rather than both potassium nitrate and polyphosphate source. The comparative compositions are otherwise formulated substantially as shown in the above table. It is found that that the concentration of total stannous in each of the comparative compositions is less than 50% at the end of the aging study.

Example 7—Transparent Dentifrice Formulations

It was further found unexpectedly that compositions made according to the present disclosure, especially toothpaste or gel compositions, are surprisingly translucent. Without being bound by theory, it is believed that the presence of un-solubilized stannous ion in a high-water dentifrice may contribute significantly to opacity. It therefore believed that the solubilization of stannous ion according to the present disclosure (by interaction with nitrate and polyphosphate ions) removes this impediment to clarity and transparency. As a result, a properly formulated dentifrice composition according to the present disclosure can achieve substantial improvements in clarity and transparency compared to prior art dentifrice compositions.

To demonstrate this, two sample compositions are prepared according to the table below.

|  | M | N | O | P |
| --- | --- | --- | --- | --- |
| Water | Q.S. (~30) | Q.S. (~30) | Q.S. (~27) | Q.S. (~30) |
| Nonionic polymers | 2 | 3 | 2 | 2 |
| Xanthan Gum | 0 | 0 | 0 | 0.4 |
| Carboxymethyl cellulose | 0.52 | 0.48 | 0.52 | 0 |
| Stannous Fluoride | 0.454 | 0.454 | 0.454 | 0.454 |
| Potassium Nitrate | 0.5 | 1.2 | 0.5 | 0.5 |
| TSPP | 1.2 | 1.2 | 1.2 | 1.2 |
| Humectants | 47 | 47 | 40 | 43 |
| Silicas | 16 | 16 | 23 | 23 |
| Anionic surfactant | 1.5 | 1.5 | 1.5 | 1.5 |
| Zwitterionic surfactant | 1.25 | 0 | 1.25 | 1.25 |
| Flavors, Colors, and other Minors | 1.4 | 1.4 | 1.4 | 1.4 |

Turbidity for the dentifrices of Example M, N, O and P is tested on a Hach-2100Q portable turbidimeter. Turbidity is expressed on a scale from 0 to 1000 NTU, wherein 0 represents complete optical clarity. Transmittance for the dentifrices is tested on a Turbiscan LAB stability analyzer as percent of light transmitted (100% is optical clarity). It is noted that both turbidity and transmittance are dependent on the path length through the sample tested (turbidity and transmittance being linearly proportional to path length for homogenous samples). While the dentifrice squeezed out of a toothpaste tube forms a ribbon having a thickness of 7-10 mm, the instruments used require filling a sample cube having a 24.8 mm path length with the tested composition. As a result, values obtained for transmittance and turbidity are depressed compared to the values that would be achieved in practice (i.e., samples M and P have a highly translucent appearance as 7-10 mm thick cylindrical ribbons). The data results are shown in the table below.

|  | M | N | O | P |
| --- | --- | --- | --- | --- |
| Turbidity (0-1000 NTU) | 126 | 201 | >1000 | 80 |
| Transmittance (%) | 21 | 7 | 0.6 | 23 |

The results show that both the formulas of Examples M and P have surprisingly high levels of clarity and transparency at the path length measured. In contrast, the formulas of Example N and O have substantially lower clarity and transparency.

What is claimed is:

1. A single-component oral care composition comprising
   (i) stannous fluoride or stannous chloride;
   (ii) a water-soluble nitrate salt, wherein the water-soluble nitrate salt is potassium nitrate;
   (iii) a water-soluble alkali metal polyphosphate, wherein the water-soluble alkali metal polyphosphate salt is tetrasodium pyrophosphate;
   (iv) more than 10% water, by weight of the composition; and;
   wherein the amount of potassium nitrate and tetrasodium pyrophosphate is effective to stabilize the stannous fluoride or stannous chloride.

2. The composition of claim 1, wherein the composition comprises a molar ratio of tetrasodium pyrophosphate to stannous fluoride or stannous chloride of at least 1:1.

3. The composition of claim 1, wherein the composition comprises a molar ratio of potassium nitrate to stannous fluoride or stannous chloride of at least 0.3:1.

4. The composition of claim 1, wherein the composition comprises from 0.1 to 2% stannous fluoride or stannous chloride, by weight of the composition; and wherein the composition comprises from 0.1 to 5% of potassium nitrate, by weight of the composition; and wherein the composition comprises from 0.1 to 5% of the tetrasodium pyrophosphate, by weight of the composition.

5. The composition of claim 1, wherein the composition comprises from 50% to 95% water, by weight of the composition.

6. The composition of claim 5, wherein the composition comprises 70% to 95% water, by weight of the composition.

7. The composition of claim 1, wherein the composition comprises from 10% to 50% water, by weight of the composition.

8. The composition of claim 1, wherein the composition comprises one or more humectants in a net amount of not more than 25% by weight of the composition.

9. The composition of claim 1, wherein the composition is a single-phase composition.

10. The composition of claim 1, wherein the composition is a dual phase composition.

11. The composition of claim 1, wherein the composition is a mouthwash.

12. An oral care package comprising a composition according to claim 1, wherein the package comprises a container comprising a single storage compartment, which compartment contains the composition, and a closure which seals the compartment.

13. A method of treatment or prevention of gingivitis, plaque, dental caries, and/or dental hypersensitivity, the method comprising the application to the oral cavity of a person in need thereof, of a composition according to claim 1.

14. A method of stabilizing stannous ion in an aqueous oral care composition comprising the steps of (1) providing an aqueous vehicle, (2) adding to the aqueous vehicle stannous fluoride or stannous chloride, (3) adding to the aqueous vehicle potassium nitrate, (4) adding to the aqueous vehicle tetrasodium pyrophosphate, wherein the final composition is a single-component high-water composition; and
   wherein the amount of potassium nitrate and tetrasodium pyrophosphate is effective to stabilize the stannous fluoride or stannous chloride.

15. The composition of claim 1, wherein the composition comprises about 0.45% by weight of stannous fluoride, 0.1-1% by weight of potassium nitrate, and 0.8-2% by weight of tetrasodium pyrophosphate.

* * * * *

UNITED STATES PATENT AND TRADEMARK OFFICE
CERTIFICATE OF CORRECTION

PATENT NO. : 10,918,580 B2
APPLICATION NO. : 16/840857
DATED : February 16, 2021
INVENTOR(S) : Shaoyi Zhang et al.

Page 1 of 1

It is certified that error appears in the above-identified patent and that said Letters Patent is hereby corrected as shown below:

In the Claims

In Column 24, Line 34, in Claim 1, "and;" should be changed to --and--.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*